United States Patent [19]
Kosmeder, II et al.

[11] Patent Number: 6,046,231
[45] Date of Patent: Apr. 4, 2000

[54] USE OF 4'-BROMOFLAVONE IN A CANCER CHEMOPREVENTATIVE COMPOSITION AND METHOD

[75] Inventors: Jerome W. Kosmeder, II, Oak Park; Robert M. Moriarty, Chicago; John M. Pezzuto, River Forest; Lynda Li Song, Arlington Heights, all of Ill.; Richard C. Moon, Plant City, Fla.

[73] Assignee: The Board of Trustees of the University of Illinois, Urbana, Ill.

[21] Appl. No.: 09/273,203

[22] Filed: Mar. 19, 1999

Related U.S. Application Data

[60] Provisional application No. 60/079,393, Mar. 26, 1998.
[51] Int. Cl.$^7$ ................................................. A61K 31/35
[52] U.S. Cl. ................................................. 514/456
[58] Field of Search ............................................ 514/456

[56] References Cited

U.S. PATENT DOCUMENTS

| | | | |
|---|---|---|---|
| 5,116,954 | 5/1992 | Brief et al. | 514/75 |
| 5,411,986 | 5/1995 | Cho et al. | 514/514 |
| 5,703,130 | 12/1997 | Han et al. | 514/616 |

OTHER PUBLICATIONS

Lu et al., Biochem. Pharmacol., 51(8), 1077–87, Abstract Only, 1996.

O.J. Plescia et al., "Subversion of immune system by tumor cells and role of prostaglandins," *Proc. Nat. Acad. Sci., USA*, vol. 72, No. 5, pp. 1848–1851, May, 1975.

M.B. Sporn et al., "Chemoprevention of cancer with retinoids," *Federation Proceedings*, vol. 38, No. 11, 2528–2534, Oct., 1979.

T.V. Zenser et al., "Prostaglandin H Synthase–catalyzed activation of benzidine: a model to assess pharmacologic intervention of the initiation of chemical carcinogenesis," *J. Pharmcol Exp. Ther.*, vol. 227, No. 3, 545–550, 1983.

D. Wild et al., Prostaglandin H synthase–dependent mutagenic activation of heterocyclic aromatic amines of the IQ–type, *Carcinogenesis*, vol. 8, No. 4, 541–545, 1987.

Y.F. Lu et al., *Biochemical Pharmacology*, 51, 1077–1087 (1996).

J.S. Goodwin, "Immunologic effects of nonsteroidal anti–inflammatory drugs," *Am. J. Med.*, 77, 7–15, 1984.

*Primary Examiner*—Jerome D. Goldberg
*Attorney, Agent, or Firm*—Marshall, O'Toole, Gerstein, Murray & Borun

[57] ABSTRACT

A composition and method of cancer chemoprevention is disclosed. The composition and method utilize 4'-bromoflavone as a cancer chemo-preventative agent in mammals, including humans.

18 Claims, 7 Drawing Sheets

USE OF 4'-BROMOFLAVONE IN A CANCER CHEMOPREVENTATIVE COMPOSITION AND METHOD

CROSS-REFERENCE TO RELATED APPLICATIONS

This application claims benefit of U.S. Provisional Application No. 60/079,393 filed Mar. 26, 1998, the disclosure of which is incorporated herein by reference.

This invention was made with government support under P01 CA48112 awarded by the National Cancer Institute.

FIELD OF THE INVENTION

The present invention relates to cancer chemopreventive compositions and methods. More particularly, the present invention relates to cancer chemoprevention in mammals, including humans, utilizing 4'-bromoflavone as a cancer chemopreventive agent.

BACKGROUND OF THE INVENTION

Cancer claims over six million lives each year worldwide and is the largest single cause of death in both men and women. Extrinsic factors, including personal lifestyles, play a major role in the development of most human malignancies. Cigarette smoking, consumption of alcohol, exposure to synthetic and naturally occurring carcinogens, radiation, drugs, infectious agents, and reproductive and behavioral practices are widely recognized as important contributors to the etiology of cancer.

A surprising conclusion is that the human diet plays a causative role in more than one-third of human neoplasia. However, the human diet not only contains numerous mutagens and carcinogens, but also contains a variety of chemicals that block carcinogenesis in animal models. Chemoprevention, i.e., the prevention, delay, or reversal of carcinogenesis through ingestion of dietary or pharmaceutical agents, therefore, is one of the most direct ways to reduce cancer-related morbidity and mortality. See, M. B. Sporn, *Fed. Proc.*, 38, 2528 (1979).

Dietary modifications can modulate cancer risk in various ways. For example, changes in caloric intake, altering the consumption of nutritive and nonnutritive diet components, and providing exposure to numerous minor chemicals that may be genotoxic or protective can increase or decrease the risk of cancer. Modifying the human diet to reduce the risk of cancer requires the identification of dietary carcinogens and chemopreventatives, even though interactions between the factors that modulate cancer risk are complex. Whereas extensive efforts have been made to identify dietary carcinogens and mutagens, the identification of chemopreventative agents has received less attention.

A large number of potential chemopreventive agents are known, some of which have proven effective in clinical trials. These agents function in a variety of mechanisms, and are directed at all major stages of carcinogenesis.

Cancer chemopreventive agents include nonsteroidal antiinflammatory drugs (NSAIDs), such as indomethacin, aspirin, piroxicam, and sulindac, all of which inhibit cyclooxygenase, abbreviated hereafter as COX. COX inhibitory activity is important in cancer chemoprevention because COX catalyzes the conversion of arachidonic acid to proinflammatory substances, such as prostaglandins, which can stimulate tumor cell growth and suppress immune surveillance. O. J. Plescia et al., *Proc. Natl. Acad. Sci. U.S.A.*, 72, 1848 (1975), and J. S. Goodwin, *Am. J. Med.*, 77, 7 (1984). In addition, COX can activate carcinogens to forms that damage genetic material. T. V. Zenser et al., *J. Pharmacol. Exp. Ther.*, 227, 545 (1983), and D. Wild et al., *Carcinogenesis*, 8, 541 (1987).

Another promising pathway for preventing chemicalinduced carcinogenesis is to alter tumor initiation through the induction of phase II detoxification enzymes and the elevation of intracellular glutathione (GSH) levels. Phase II enzymes, such as quinone reductase (QR) and glutathione S-transferase (GST), are a group of inducible enzymes responsible for facilitating the removal of xenobiotics from animals and humans. QR protects cells against the cytotoxicity of quinones by promoting obligatory two-electron reductions of quinones, thereby preventing their participation in oxidative cycling and interaction with critical nucleophilies. GST detoxifies by catalyzing the conjugation of GSH to various reactive electrophiles which decrease the availability of reactive electrophiles to bind to DNA and possibly initiate the transformation process. GSH, as the principal intracellular nonprotein thiol compound, functions as cosubstrate for GST-catalysed conjugation of electrophilic chemicals. Chemopreventive activity of phase II enzyme inducers can be achieved by modification of carcinogen metabolism, increasing carcinogen excretion, and decreasing carcinogen DNA interactions.

Several chemopreventive compounds have been identified solely on the basis of their ability to induce phase II enzymes in laboratory animals and cell cultures. Similarly, during our study directed to identifying novel chemopreventive compounds, cultured Hepa 1c1c7 cells were used to evaluate the potential of compounds to enhance QR activity. This study led to the identification of various active agents, including brassinin, withanolides, and sulforamate. In addition, as exemplified by our work with Tephrosia purpurea, some novel flavonoids were found to act as potent phase II enzyme inducers.

Compounds that induce phase II detoxification enzymes have been shown to protect against carcinogen-initiated cancer. Inducers of phase I enzymes, such as cytochrome P450 isozymes, are required for metabolic disposal of xenobiotics, but also are considered a cancer risk factor because of their potential to activate procarcinogens and increase the carcinogenicity of various compounds. Evidence of phase I induction of cytochrome P-4501A1 isozyme by 4'-bromoflavone was disclosed in Y. F. Lu et al., *Biochemical Pharmacology*, 51, pages 1077–1087, (1996).

Compounds that elevate phase I and phase II enzymes are classified as bifunctional inducers. Monofunctional inducers selectively elevate phase II enzymes. Sulforaphane, a compound isolated from broccoli, was reported as the most potent monofunctional inducer of phase II enzymes, but the compound is toxic, and difficult and very expensive to synthesize. Cho et al. U.S. Pat. No. 5,411,986 discloses several analogs of sulforaphane that induce phase II enzymes and may be useful as chemoprotective agents. Han et al. U.S. Pat. No. 5,703,130 discloses chalcone retinoids having biological activity on cancer or precancer cells. Briet et al. U.S. Pat. No. 5,116,954 discloses flavonic compounds having anticancer activity.

There still is a need in the art, however, for the identification of compounds that have a cancer chemopreventative effect on mammals. Such cancer chemopreventative compounds then can be used in drug compositions or as food additives to reduce the risk of cancer. To this end investigators have searched for new cancer chemopreventative agents by evaluating hundreds of plant extracts for a potential to induce phase II enzymes. There also is a need to find synthetic chemopreventative compounds having a low toxicity, and that can be synthesized easily and economically to provide useful amounts of the compounds.

SUMMARY OF THE INVENTION

The present invention is directed to cancer chemopreventative agents, compositions, and methods of using the chemopreventative agents to prevent carcinomas. In particular, the present invention is directed to 4'-bromoflavone and compositions containing 4'-bromoflavone, and use of 4'-bromoflavone and the compositions in methods of cancer chemoprevention.

An important aspect of the present invention, therefore, is to provide a method and composition for preventing tumor growth using 4'-bromoflavone.

Another important aspect of the present invention is to provide a method and composition to suppress the initiation of a cancer using 4'-bromoflavone.

Another aspect of the present invention is to overcome the problem of high mammalian toxicity and high cost associated with prior cancer chemopreventative agents by using 4'-bromoflavone.

Still another aspect of the present invention is to overcome the problem of insufficient availability associated with anticancer agents by utilizing readily synthesized 4'-bromoflavone, which can be synthesized in commercial quantities, and then can be used in compositions and methods of cancer chemoprevention.

Yet another important aspect of the present invention is to provide a food product, or a food supplement, that contains 4'-bromoflavone and can be used in methods of cancer chemoprevention.

Another important aspect of the present invention is to provide a drug composition containing 4'-bromoflavone, and that can be administered, preferably orally, to chemoprevent carcinomas.

These and other aspects of the present invention will become apparent from the following detailed description of the preferred embodiments of the invention.

DETAILED DESCRIPTION OF THE PREFERRED EMBODIMENTS

Previous studies suggested that induction of phase II detoxification enzymes, such as quinone reductase (QR) and glutathione S-transferase (GST), is a mechanism for cancer chemoprevention. Various compounds, such as dithiolethione, sulforaphane, indole-3-carbinol, ethoxyquin, and βNF (β-naphthoflavone, have been reported to exert broad-based anticarcinogenic activity against a variety of chemical carcinogens at multiple target sites in animal models via induction of phase II detoxification enzymes. As a group, these inducible phase II enzymes facilitate the metabolic detoxification of xenobiotics in mammals, and can achieve chemopreventive activity by modification of carcinogen metabolism through increased carcinogen excretion and decreased carcinogen-DNA interactions.

Consequently, identifying potent phase II enzyme inducers has been used as a strategy to discover potential chemopreventive agents. Using a QR induction assay in Hepa 1c1c7 hepatoma murine cells and its mutants, bioassay-guided fractionation of *T.purpurea* led to the isolation and identification of a group of flavonoids as potent QR inducers.

Flavonoids encompass a diverse array of compounds that are widely distributed in the plant kingdom. Naturally occurring plant flavonoids, and related synthetic analogs, exhibit a broad spectrum of biological actions in mammals, such as anti-allergic, anti-inflammatory, antioxidant, gastroprotective, antiviral, toposomerase II inhibitory, protein kinase C-inhibitory, antimutagenic, and anticarcinogenic actions.

Certain naturally occurring flavonoids were found to induce phase II enzymes. Accordingly, over 100 natural and synthetic flavonoids were investigated for an ability to induce phase II enzymes. In particular, several classes of flavonoids (e.g., flavones, flavanones, and chalones) have been identified as potent inducers of phase II enzymes in vitro and in vivo. In this study, 4'-bromoflavone was identified as one of the most potent inducers of phase II enzymes. 4'-Bromoflavone not only highly induced quinone reductase (QR) activity in Hepa 1c1c7 murine hepatoma cells (CD (concentration to double activity): 0.01 $\mu$M), but also effectively induced the α- and $\mu$-isoforms of glutathione S-transferase in cultured H4IIE rat hepatoma cells with no observed toxicity. In short-term dietary studies, 4'-bromoflavone (i.e., 4'-BF) also significantly increased QR activity and glutathione levels in female Sprague-Dawley rat liver, mammary gland, colon, stomach, and lung, in a dose-dependent fashion (P<0.0001).

In general, compounds that induce phase II detoxification enzymes have been shown to protect against carcinogen-initiated cancer, whereas inducers of phase I enzymes have been suggested to increase the carcinogenicity of some compounds. Compounds which induce detoxification enzymes have shown efficacy in preventing the initiation of cancer by known carcinogens, as well as protecting against toxicity from drug overdosing and chemotherapeutics. Sulforaphane was reported as the most potent monofunctional inducer of phase II enzymes (CD=0.23 μM), but is difficult and very expensive to synthesize (e.g., 100 g/$50,000). 4'-Bromoflavone is a bifunctional inducer, and is significantly more potent (CD=0.01 μM) than sulforaphane with respect to inducing phase II enzymes. In addition, due to the structural simplicity of the compound, 4'-bromoflavone is economical and easy to synthesize (e.g., 100 g/$200) and is much less toxic ($IC_{50} \geq 166$ μM) than sulforaphane. The closest bifunctional inducer of detoxification enzymes to 4'-bromoflavone is β-naphthoflavone, which has a CD=0.02–0.04 μM, and is considerably more toxic ($IC_{50}$=8 μM) and expensive to synthesize (100 g/$1,600) than 4'-bromoflavone.

4'-Bromoflavone is a known compound which is an extremely potent inducer of phase I and phase II detoxification enzymes. 4'-Bromoflavone is known to significantly increase levels of cytochrome P-4501A1, a phase I enzyme, but, as illustrated hereafter, it also substantially increased glutathione (GSH), glutathione-S-transferases (GSTs), and quinone reductase (QR) both in vitro and in vivo. 4'-Bromoflavone also has shown an ability to inhibit 7,12-dimethylbenz[a]anthracene (DMBA) induced mammary carcinogenesis in animals.

4'-Bromoflavone is readily synthesized using reactions well known to persons skilled in the art. The following is a simple and economical route for providing commercial quantities of 4'-BF, wherein KOH is potassium hydroxide, MeOH is methanol, and DMSO is dimethyl sulfoxide:

4'-Bromoflavone
(4'-BF)

The structures of β-naphthoflavone and sulforaphane are provided for comparison:

β-Naphthflavone
(Bifunctional inducer)

Sulforaphane
(Monofunctional inducer)

As shown in the above synthetic scheme, (E)-4-bromo-2'-hydroxychalcone was prepared from 2'-hydroxyacetophenone and 4-bromobenzaldehyde via a base-catalyzed Claisen-Schmidt condensation. 4'-BF subsequently was formed by oxidative cyclization with catalytic iodine in DMSO. In this manner, 4'-BF can be produced on a scale (overall yield of 70%) at a cost of less than $2/g.

In the present studies, the induction potencies of over 100 flavonoids on QR activity was tested in a QR induction assay in Hepa 1c1c7 murine hepatoma cells. This test was used because the specific activity of QR rises concomitantly with other phase II enzymes in many animal tissues in response to various chemopreventive agents. The study included natural and synthetic B-ring substituted flavones, as well as biosynthetic precursor chalcones and flavanones.

These studies showed the significant inducing capacity and the low toxicity of 4'-BF. The induction potency of 4'-BF on QR activity and GSH levels was further confirmed in rat tissues in multiple organ sites. A dose and time dependent induction of two major detoxification isoforms of GST (α form and μ form) mediated by 4'-BF has been studied in H4IIE rat hepatoma cells. In order to determine a possible mechanism of induction, the QR mRNA expression was tested using a RT-PCR technique and the induction patterns using HepG2 cells transfected with QR-chloramphenical acetyltransferase plasmid constructs containing various portions of 5'-region of the QR gene were analyzed. The antimutagenic activity of 4'-BF was tested in an antimutagenic assay against DMBA-induced mutagenesis with *Salmonella typhimurium* strain TM677. The chemopreventive efficacy of 4'-BF also was evaluated in a DMBA-induced mammary tumor carcinogenesis model in Sprague Dawley rats.

In the tests described hereafter, the results revealed that induction was regulated at the transcriptional level. Moreover, 4'-BF strongly inhibited DMBA-induced mutagenesis with *Salmonella typhimurium* strain TM677. Corresponding to the significant chemopreventive effects of 4'-BF in the in vitro study, a surprising and unexpected chemopreventive effect of 4'-BF was also illustrated in an in vivo study. 4'-BF significantly inhibited the incidence and multiplicity of mammary tumors, and greatly increased the tumor latency (P<0.001) in the DMBA-induced mammary tumor carcinogenesis model in female Sprague-Dawley rats. Taken together, the test results demonstrate that 4'-BF is an excellent cancer chemopreventive agent.

The following materials and methods were used to test 4'-BF and other flavonoids:

Chemicals and Cell Cultures. All chemicals, unless specified, were purchased from Sigma Chemical Co. or Aldrich Chemical Co., Milwaukee, Wis. All cell culture media and supplements were obtained from Life Technologies, Grand Island, N.Y. Hepa 1c1c7 murine hepatoma cells and its mutants, and HepG2 human hepatoma cells, were cultured as described in C. Gerhauser, *Cancer Research*, 57, pp. 272–278 (1997). H4EII rat hepatoma cells were grown in minimal essential medium (MEM), without ribonucleosides or deoxyribonucleosides, containing 100 units/ml penicillin G sodium, 100 units/ml streptomycin sulfate, and 250 ng/ml amphotericin B supplemented with 5% fetal calf serum at 37° C. in an atmosphere of 5% carbon dioxide ($CO_2$) in a humidified incubator. MCB7 human breast carcinoma cells (American Type Culture Collection) were maintained with Earle's MEM supplemented with 10 mg/liter insulin, antibiotic, antimycotic (1×), nonessential amino acids (1×), sodium pyruvate (1×), and 10% fetal bovine serum (37° C., 5% $CO_2$).

Synthesis of 4'-Bromoflavone. 4'-BF was synthesized using the sequence outlined above. In particular, 2'-hydroxyacetophenone (79.48 g, 72.0 ml, 584 mmol) and 4-bromobenzaldehyde (100.00 g, 520 mmol) were dissolved in methanol (1.0 liter) with stirring. Potassium hydroxide (89.60 g, 1.60 mol) was added in portions to give a blood-red solution that was stirred for 6 hours, during which 4-bromo2'-hydroxychalcone precipitated as the potassium salt. The solution/suspension was poured into cold 1 N HCl (500 ml), and further concentrated HCl was added until the solution was acidic. The resulting yellow precipitate was filtered, washed with water (1 liter), and recrystallized from methanol to give 138.53 g (85%) as yellow crystals: mp 145–147° C. [lit. 146–148° C.]. $^1$H NMR (400 MHz, $CDCl_3$); δ6.93 (ddd, J=8.1, 7.1, 0.9 Hz, 1H H-5'), 7.01 (dd, J=8.3, 1.0 Hz, 1H, H-3'), 7.46–7.52 (m, 2H, H-2, 6, –4'), 7.60 (d, J=15.4 Hz, 1H, H-α), 7.80 (d, J=15.5 Hz, 1H, H-β), 7.87 (dd, J=8.1, 1.6 Hz, 1H, H-6'), 10.26 (s, 1H, 2'-OH); $^{13}$C NMR (100 MHz, $CDCl_3$), δ118.59, 118.85, 119.81, 120.50 (C-α), 125.19, 129.54, 129.89, 132.20, 133.37, 136.49, 143.88 (C-β), 163.53 (C-2'), 193.31 (C=O).

The chalcone was converted to 4'-bromoflavone through adaptation of the procedure of Doshi et al., *J. Ind. Chem.*, 25B, p. 759 (1986). 4-Bromo-2'-hydroxychalcone, 138.53 g. 457 mmol) was dissolved in DMSO (1 liter) to which a catalytic amount of iodine (11.60 g, 45.7 mmol) was added. The solution was refluxed for 4 hours with monitoring by TLC. The solution was cooled to room temperature and poured into saturated aqueous sodium thiosulfate (1 liter), and the resulting precipitate was filtered, washed with cold water, and recrystallized twice from dichloromethane-methanol to give 114.27 g (70%) of colorless crystals: mp 177–179° C. (lit. 177–178° C.); $^1$H NMR (400 MHz, $CDCl_3$): δ6.80 (s, 1H, H-3), 7.43 (ddd, J=8.0, 6.9, 0.8 Hz, 1H, H-6), 7.56 (br d, J=8.5 Hz, 1H, H-8), 7.66 (app d, J=8.6 Hz, 2H, H-2', –6'), 7.71 (ddd, J=8.7, 7.2, 1.7 Hz, 1H, H-7), 7.79 (app d. J=8.6 Hz, 2H, H-3', –5'), 8.22 (dd, J=8.0, 1.5 Hz, 1H, H-5); $^{13}$C NMR (100 MHz, $CDCl_3$): δ107.70, 118.02, 123.91, 125.36, 125.73, 126.28, 127.67, 130.70, 132.33, 133.89, 162.26 (C-8a), 178.21 (C-4).

Determination of Quinone Reductase Activity in Cell Cultures. To determine the potency of inducers, Hepa 1c1c7 murine hepatoma cells as described in the Gerhauser publication were placed in 96-well plates at a density of $1\times10^4$ cells/ml in 200 μl of medium. After a preincubation period of 24 hr, the media were decanted and 190 μl fresh media were added to each well. Ten (10) μl test agents dissolved in 10% DMSO (final concentration of DMSO is 0.5%) with a serial 2-fold dilutions were introduced to each well, and the plates were incubated for an additional 48 hours. Specific QR activity was determined by measuring the NADPH-dependent menadiol-mediated reduction of 3-(4, 5-dimethylthiazo-2-yl)-2,5-diphenyltetrazolium bromide to blue formazan formed per mg protein per minute. Protein was determined in an identical set of test plates by staining with crystal violet. Hepa 1c1c7 cells retain many characteristics of normal issues, particularly the capacity for carcinogen activation and metabolism. They are amenable to precise control of environmental, nutritional, and hormonal factors. Additional testing in two mutant cell lines derived from wild-type Hepa 1c1c7 cells, TAOBP$^r$cl and BP$^r$cl, which are either defective in a functional arylhydrocarbon receptor or unable to translocate the receptor-ligand complex to the nucleus, respectively, according to the protocol outline above, allowed definition of mono- and bifunctional inducers. Induction of QR activity was calculated by comparing the QR specific activity of agent-treated cells with that of solvent-treated cells, and a plot of ratio was generated. CD represents the concentration required to double QR induction. Chemopreventive index (CI) is an indexing value generated by comparing CD with $IC_{50}$ (concentration for 50% inhibition of cell viability) values.

Analysis of Quinone Reductase Activity and Glutathione Level in Rat Tissues. Spraque Dawley rats (n=10) at 43 days of age were placed on an appropriate experimental diet (5000, 2500, 1250, 625, and 312.5 mg/kg diet of 4'-BF) for three weeks. After three weeks, animals were sacrificed by carbon dioxide ($CO_2$) asphyxiation. The livers, mammary glands, colons, stomachs, and lungs were collected, rinsed with saline, and frozen in liquid nitrogen and stored at −80° C. until enzyme activities were determined. Individual tissues (except mammary glands) were homogenized in 0.25 M sucrose and centrifuged at 15,000×g for 30 min at 4° C. The supernatant fluids were collected, 20% volume of 0.1 M $CaCl_2$ in 0.25 M sucrose were added. After incubation at 0° C. for 30 min and further centrifuging at 15,000×g for 30 min at 4° C., a clear cytosolic fraction was used for enzyme assay. Mammary glands of each animal were pooled, homogenized in 1 ml ice-cold 0.1 M phosphate buffer pH 6.5 and centrifuged (15,000×g, 30 min at 4° C.), a clear supernatant suitable for enzyme assay resulted. Dicumarol-sensitive QR activity was measured in duplicate in 50 μl of suitable dilution of the tissue supernatant as described for the cellular system. GSH levels were assayed in duplicate using 96-well plates. The assayed utilized 40 μl of suitable diluted tissue homogenate mixed with 170 μl of a freshly prepared reaction mixture containing 20 μl 6 mM 5,5'-dithiobis-(2-nitrobenzoic) (DTNB) in stock buffer (125 mM phosphate buffer, pH 7.5, 6.3 mM EDTA), 10 μl glutathione reductase solution (50 units in 10 ml stock buffer) and 140

μl of a NADPH-generating system (2.5 ml of 0.5 Tris-Cl buffer, pH 7.4, 33 mg of bovine serum albumin, 330 μl of 1.5% TWEEN 20, 330 μl of 150 mM glucose 6-phosphate, 30 μl of 50 mM $NADP^+$, 100 U of yeast glucose 6-phosphate dehydrogenase, and distilled water to a final volume of 50 ml). The plates were shaken for 5–10 min and the extent of 2-nitro-5-thiobenzoic acid formation was monitored at 405 nm. A GSH standard curve was used to calculate the GSH content. GSH levels were expressed as nmol/mg protein.

Western Blot Analysis Glutathione S-transferase Expression. Cultured H4IIE rat hepatoma cells were treated with test agent with various concentrations or various time points. These cells were shown to express GSTα and GSTμ, the two major detoxification isoforms in liver. Cells were harvested using SDS lysis buffer (20 mM Tris-Cl, pH 6.8, containing 0.4% SDS (w/v), 4% glycerol, 0.24 M β-mercaptoethanol, and 0.5% bromphenol) and the lysates were boiled for 5 minutes, then stored at −20° C. An aliquot of lysate was used for protein determination using a bicichoninic acid protein assay kit with BSA as a standard. Equivalent amounts of protein were electrophoresed by SDS-PAGE on precast 12.5% Tris-glycine acrylamide gels (Novex, San Diego, Calif.), then transferred to polyvinylidene difluoride (PDVF) membranes. Nonspecific binding sites were blocked with 10% nonfat dry milk and blotting was performed with goat polyclonal antirat GSTYa (α class) IgG or antirat, GSTYb (μ class) IgG and analyzed by alkaline phosphatase-conjugated antigoat IgG secondary antibody (Oxford Biomed Research, Inc.) and quantified using an AP 20 Alkaline Phosphatase Kit detection system (Oxford Biomed Research, Inc.).

Transcient Transfection Gene Expression Assay. Cultured HepG2 human hepatoma cells were transfected with three plasmid constructs (PDTD-1697CAT, XRE-CAT, ARE-CAT) containing various portions of the 5'-region of the QR gene fused to the CAT gene using the calcium phosphate precipitation method (J. Sambrook et al., *Molecular cloning: A Laboratory Handbook*, Ed. Chris Nolan, CHS Laboratory Press, 1989). After 4 hours of transfection, the cells were treated with 10% glycerol for 3 minutes and rinsed with PBS and switched to MEM, containing 100 units/ml penicillin G sodium, 100 units/ml streptomycin sulfate, nonessential amino acids, and 1 mM sodium pyruvate (Life Technologies Inc.) supplemented with 10% fetal bovine serum for 12–16 hours recovery. Then, test agents were added to the cells. After 48 hours of treatment with the test agents, cells were harvested with lysis buffer (Boehringer Mannheim Biochemical) and CAT protein expressions were assessed using a CAT ELISA kit (Boehringer Mannheim Biochemical). CAT enzyme expression was normalized for the protein content of each sample. All data were expressed as mean +/− SD. Means were compared using Student's t test with n=4.

RT-PCR Analysis of QR mRNA Expression. Primers were designed based on rat QR gene and custom synthesis. Total RNA was isolated from cultured Hepa 1c1c7 cells with TRIzol® reagent (Life Technologies, Inc.) and quantified using a UV-spectrometer. The reverse transcription of RNA was performed in a final volume of 20 μl containing 5× First Strand Synthesis Buffer (Life Technologies, Inc.), 5 mM $MgCl_2$, 1 mM of each dNTPs, 1 unit Rnase inhibitor (Life Technologies, Inc.), 2.5 units SuperScript II reverse transcriptase (Life Technologies, Inc.), 2.5 μM oligo $(dT)_{16}$, 0.2 μg total RNA, and DEPC-treated water. After incubation at 47° C. for 30 min, the RT-reaction was terminated by heating to 70° C. for 15 minutes. To the newly synthesized cDNA (1 μL), a PCR reaction mixture (Advantage KlenTaq polymerase Mix, CloneTech) containing 3 mM $MgCl_2$, 2.5 units Taq polymerase, 6 pmol of primers for QR gene (5'-CGAATCTGACCTCTATGCTA-3'; and 3 pmol of primers for β-actin, 5'-CACTCTCTCAAACCAGCCTT-3'), (5'-GAGCAAGAGAGGTATCCTGA-3'; 5'-CAGCTCATAGCTCTTCTCCA-3') as internal control was added to bring the final volume to 50 μl. The PCR reaction was heated to 94° C. for 1 min and immediately cycled 27 times through a 30 second denaturing step at 94° C., a 45 second annealing step at 55° C., a 60 second elongation step at 72° C. with Perkin Elmer 2400 themocycler. Following the final cycle, a 5 minute elongation step at 72° C. was performed. Aliquots of the PCR product were electrophoresed on 2.5% agarose gels (Life Technologies, Inc.), and PCR fragments were visualized with ethidium bromide staining, quantified by scanning densitometry, and expressed as folds increase after normalization to β-actin gene expression.

Inhibition of DMBA-induced Mammary Carcinogensis in Rats. On the basis of a 3-week feeding study, maximum tolerated doses were evaluated, and suitable doses were selected for the study of inhibition of DMBA-induced mammary carcinogenesis in rats. Virgin, female Sprague Dawley rats were obtained from Harlan/Sprague-Dawley at 35 days of age. All animals were placed on a diet of Teklad 4% Rat/Mouse chow at this time. After a quarantine period of 1 week, at 42 days of age, the animals were randomized by weight into six groups and placed on the appropriate experimental diet containing 2000 and 4000 mg 4'-bromoflavone/kg diet. At 50 days of age, the animals received a single i.g. dose of 15 mg of DMBA in sesame oil (or vehicle only) following an overnight fast. The rats were maintained on the 4'-bromoflavone diet for one additional week, and then returned to the basal diet without test agent at 57 days of age. During the experiment, all animals were weighed weekly. Palpation for mammary tumors began 3 weeks after the animals received the DMBA, and continued until termination of the study (120 days post DMBA). The date of appearance and location of all tumors was recorded. Animals were observed twice daily to assess their general health. Moribund animals were sacrificed by $CO_2$ asphyxiation. Moribund animals or animals found dead were necropsied immediately. At the termination of the experiment, all mammary tumors were excised and weighed, and mean tumor weight was established. Tumors for Group 2–5 were frozen. The abdominal/inguinal glands of Group 8 were disected free of lymph nodes; one side was frozen, the other side was fixed. Incidence was evaluated with Fisher's exact test and the Logrank test was used for tumor incidence rate. Tumor multiplicity was calculated using Armitage's test for trends in proportions. Latency and tumor weight were evaluated by an unpaired t-test. Survival was analyzed with log-rank analysis.

Effect of 4'-Bromoflavone on DMBA-induced QR Activity and Cytochrome P4501A1 Activity in Rat Tissues. At 43 days of age, Sprague Dawley rats were placed on various experimental diets (Table 1) for 1 week prior to administration of a single (i.g.) dose of DMBA (15 mg). Animals then were weighed and sacrificed by $CO_2$ asphyxiation. Tissues (livers and mammary glands) were collected, rinsed with saline, frozen in liquid nitrogen, and stored at −80° C. until analysis. Individual tissues were homogenized in 0.05 M Tris-HCl buffer (pH 7.5) containing 0.25 M sucrose. Cytosolic and microsomal fractions were obtained through differential centrifugation. Dicumarol-sensitive QR activity was measured as described above using 50 μl of suitably diluted cytosol supernatants (in duplicate). Cytochrome P4501A1-mediated EROD activities were determined as described previously in R. Poul et al. *Anal. Biochem.*, 107, pp. 265–275 (1980) and S. Sharma et al., *Cancer Res.*, 54, pp. 5848–5844 (1994), with slight modifications using suitably diluted microsomal protein. Enzyme activities were expressed as nmol/mg protein/min. Protein content was determined using Bradford reagent with BSA as standard, and data were presented as mean ±SE and analyzed using Student's t test (n=5).

TABLE 1

Protocol for assessing the effect of 4'-BF on DMBA-induced phase I and phase II enzyme activities[1)]

| Codes | Treatments | DMBA (t 15 mg, i.g.) |
|---|---|---|
| C | Basal oil diet | — |
| DMBA | Basal Oil diet | — |
| G-1 | 312.5 mg 4'-BF/kg diet | — |
| G-2 | 625 mg 4'-BF/kg diet | — |
| G-3 | 1250 mg 4'-BF/kg diet | — |
| G-4 | 2500 mg 4'-BF/kg diet | — |
| G-5 | 5000 mg 4'-BF/kg diet | — |
| G-6 | 3125 mg 4'-BF/kg diet | — |
| G-7 | 1250 mg 4'-BF/kg diet | — |
| G-8 | 5000 mg 4'-BF/kg diet | — |

[1)]For each group, n = 5.

Inhibition of DMBA-induced Cytochrome P4501A1 Activity. Female Sprague Dawley rats (43 days of age) were treated with DMBA (i.g.), and liver microsomes were isolated through differential centrifugation. Cytochrome P4501A1 activity was monitored by assessing EROD activity. Briefly, 200 µl of microsomal protein (2 mg/ml) were added to a reaction mixture containing 640 µl of 0.05 M Tris-HCl buffer (pH 7.5), 100 µl of BSA (10 mg/ml in Tris buffer), 20 µl of 0.25 M $MgCl_2$, 40 µl of cofactor solution (0.3282 g of NADP and 1.417 g of glucose 6-phosphate in 40 ml of 1.15% KCl), 2.5 units of glucose 6-phosphate dehydrogenase, 10 µl of substrate (1 mg of ethoxyresorufin in 10 ml of methanol) and 10 µl of various concentrations of 4'-BF in DMSO (α-naphthoflavone as positive control; DMSO as negative control). After incubating at 37° C. for 4 min, the reactions were terminated by the addition of 2 ml of methanol. Samples were then centrifuged for 20 min at 2,000×g. and 200 µl of the supernatant fractions were transferred to 96-well plates and read on a spectrofluorimeter (500 nm excitation and 585 nm emission). Assays were conducted in triplicate and the percent of inhibition was calculated as: [1−(sample A-blank)/(DMSO A-blank)]×100.

Effect of 4'-BF on the Binding of Metabolically Activated [$^3$H]B[α]P to DNA of Cultured Cells. HepG2 cells or MCF-7 cells were plated at a density of 1×10$^6$ cells/dish in 6 cm Petri dishes and allowed to incubate for 18 hours. Fresh media containing test samples were added to the cells 2 hours prior to the addition of 1 µM [$^3$H]B[α]P (10 Ci/mmol) The test compound and tritiated carcinogen then were incubated for 6 hours. Following incubation, genomic DNA was extracted by the method described by Sharma et al., with minor modifications. Briefly, the cells were washed three times with PBS and harvested by incubation with 0.5 ml of proteinase K (100 µg/ml) in 0.2 M Tris-0.1 M EDTA (pH 8.5) for 10 min at 37° C. The cells were gently scraped from the dishes, transferred to 50 µl of 10% SDS solution, and incubated for 3 hours at 55° C. Following the addition of 75 µl of 5 M potassium acetate solution, the cells were placed on ice for 30 min, and centrifuged for 15 min at 13,000×g. The supernatant was transferred to a fresh tube, and 2 volumes of cold ethanol were added to precipitate the DNA overnight at −20° C. The DNA was harvested by centrifugation for 20 min at 13,000×g in an Eppendorf microfuge, and the supernatant was removed. The DNA pellet was washed with 70% ethanol and finally resuspended in 500 µl of 10 mM Tris-1 mM EDTA (pH 8.0) buffer. RNA was removed by treating with 5 µl of RNase A (10 mg/ml) and 5 µl of RNase TI (5 units/µl) at 37° C. for 1 hour. An aliquot of harvested DNA was used for measuring the relative absorbencies at 260 and 280 nm ($A_{2360}$ nm/$A_{2380}$ nm=1.7–1.9), and the DNA content was determined by absorbance at 260 nm (1 $A_{2360}$ nm unit=50 µg). The remaining sample was used for the determination of radioactivity. All experiments were performed in triplicate; percentage inhibition of carcinogen-DNA binding mediated by test samples was calculated as follows: % inhibition=[1-(dpm per µg DNA test cells/dpm per µg DNA control cells)]×100.

The above tests provided the following results, which are summarized in Tables 2 and 3:

Induction of Quinone Reductase in Hepa 1c1c7 Cells. Over 100 natural or synthetic flavonoids were tested for a potential to induce QR activity in Hepa 1c1c7 cells and two mutants. Modification of the B-ring of chalcones, flavanones, and flavones was hypothesized to induce torsion of the B-ring, and, therefor, simulate out-of-plane distortions characteristic of polycyclic aromatic hydrocarbons, such as DMBA. Induction of QR activity was calculated by comparing the QR specific activity of agent-treated cells with the QR specific activity of solvent-treated cells, and a plot of ratios was generated. CD represents the concentration required for a double fold of induction. CI (Chemopreventive Index) is a value obtained by comparing CD with $IC_{50}$ (concentration for 50% inhibition of cell viability in micrometers). As a result, fifteen synthetic flavonoids were identified as potent QR inducers in Hepa 1c1c7 cells with CD values of 0.01–1.0 µM, i.e., 3'-bromoflavone, 4'-bromoflavone, 3'-chloroflavone, 4'-chloroflavone, 3'-fluoroflavone, 2'-methoxyflavone, 2'-methoxyflavanone, 2'-hydroxy-2-methoxychalcone, 2'-hydroxy-2-methylchalcone, 2'-hydroxy-2-nitrochalcone, 2-bromo-2'-hydroxychalcone, 2'-hydroxy-2,6-dimethoxychalcone, 2'-methylflavanone, 2'-fluoroflavone, and 4'-trifluoromethylflavone, 0.1, 0.01, 0.27, 0.02, 0.67, 0.63, 0.31, 0.67, 0.30, 0.53, 0.54, 1.00, 0.80, and 0.03 µM, respectively. Among these active compounds, 4'-BF was surprising in terms of its significant inducing capacity and its low cytotoxicity. Either no or weak QR activity was induced by these compounds in the mutant cells. All of these compounds were bifuctional inducers. Sulforaphane was identified earlier as a potent inducer of QR activity in vitro and in vivo, and was used as positive control in this experiment. Compared to sulforaphane, 4'-BF is about 40 times more active, and also about 15 times less toxic.

Figure 8A:
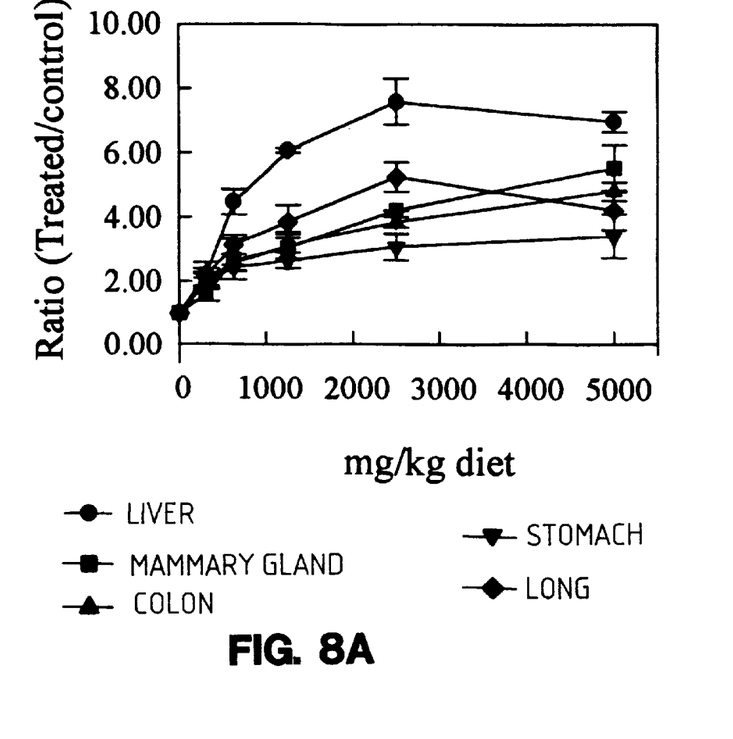
FIG. 8 contains plots for induction of QR (A) and GSH (B) mediated by 4'-BF, expressed as a ratio of induction (treated/control) vs. mg 4'-BF/kg of diet.
Figure 8B:
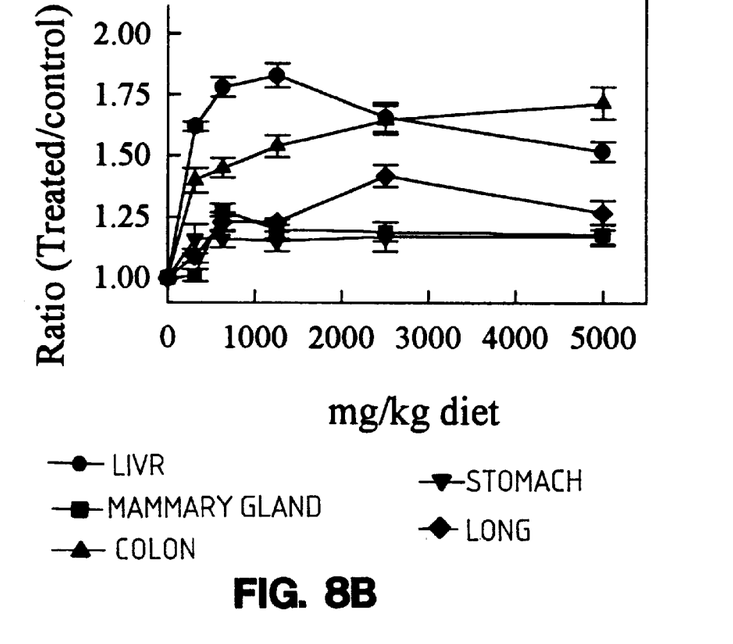

Induction of Quinone Reductase Activity and Glutathione Level in Rat Tissues. Based on the results in cell cultures, 4'-BF was further evaluated for its inducing potency in rat liver, mammary gland, colon, stomach, and lung. Dietary administration of 4'-BF to Sprague Dawley rats (312.5–5000 mg/kg diet) for 3 weeks significantly induced QR activity, i.e., 2.22–7.60 fold in liver, 1.59–5.52 fold in mammary gland, 2.09–4.81 fold in colon, 1.97–3.42 fold in stomach, and 2.18–5.25 fold in lung, respectively, as illustrated in FIG. 8. Maximum QR induction mediated by 4'-BF was observed in at a concentration of about 2500 to about 5000 mg/kg diet. Dietary administration of 4'-BF also highly increased GSH levels in multiple organ sites, i.e., 1.62–1.83 fold in liver, 1.01–1.28 fold in mammary gland, 1.40–1.72 fold in colon, 1.16–1.17 fold in stomach, and 1.09–1.42 fold in lung, respectively. The concentration of 4'-BF for maximum induction of GSH was about 1250 to about 2500 mg/kg diet, but varied for different organ sites.

Similar effects were observed with βNF, probably as a result of rapid GSH conjugation stimulated by a higher concentration of test agents. However, in addition to the liver, enzymatic and inductive events occurring in the mammary gland may be of critical importance in the genesis of breast cancer. In studies investigating the chemopreventive potential of βNF, dithiolethione, ethoxyquin, and BHA (butylated hydroxyanisole) with the DMBA-induced rat mammary carcinogenesis model, induction of phase II detoxification enzymes at the mammary level appear to be an important factor for chemopreventive efficacy, and similar factors may apply in the case of 4'-BF.

Figure 7A:
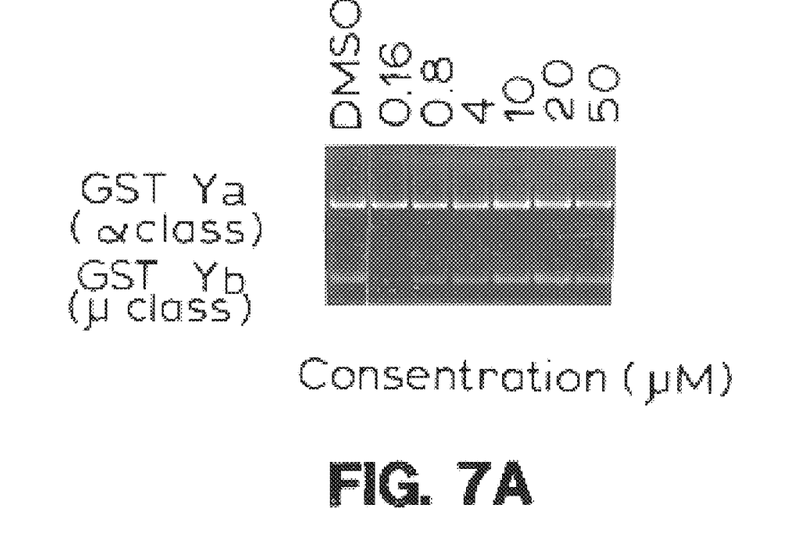
FIG. 7 shows expression of the α- and μ-isoforms of GST with cultured H4IIE cells.
Figure 7B:
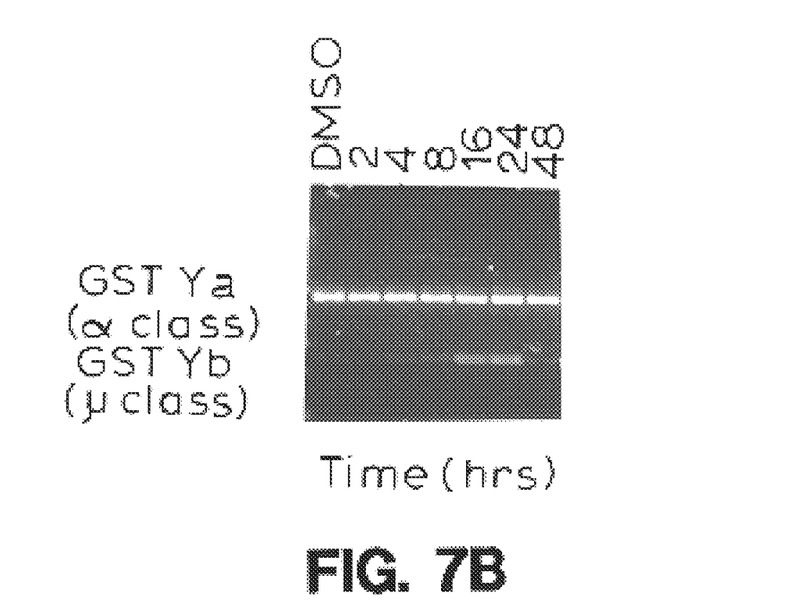

Induction of Expression of Glutathione S-transferase Ya (α-type) and Yb (μ-type) in Cell Cultures. Another important activity of 4'-BF involves enhanced expression of two major detoxification isoforms of GSTs (Ya: α class; Yb: μ class). To date, the superfamily of mammalian cytosolic GST isozymes has been defined genetically to consist of four classes; α, μ, π, and θ, which differ in tissue-specific expression and distribution, as well as substrate specificity. The major detoxification isoforms of liver, α and μ, were induced by 4'-BF in a time- and dose-dependent fashion in H4IIE rat hepatoma cells (FIG. 7). Cultured H4IIE cells were treated either with 10 μM of 4'-BF (FIG. 7B) or sulforaphane for 0, 2, 4, 8, 16, 24, and 48 hours for a time-dependent study, or with 0.16, 0.8, 4, 10, 20, and 50 μM of 4'-BF (FIG. 7A) or sulforaphane for 24 hr for a dose-dependent study (FIG. 7A). The expressions of two major detoxification isoforms of GSTs (GST Ya: α-type, and GST Yb: μ-type) mediated by 4'-BF or sulforaphane were investigated in H4EII rat hepatoma cells using Western blotting technique. Both GST Ya and GST Yb were induced by 4'-BF in a time, dose-dependent manner with similar profile. Maximum induction time was in a range of 16–24 hours, whereas maximum induction concentration appeared to be 10–20 μM. Time, dose-dependent induction of GST Ya and GST Yb mediated by sulforaphane were observed in H4EII cells as well. Maximum induction time was in a range of 16–24 hours, whereas maximum induction concentration was about 4–10 μM. Unlike 4'-BF, a declined induction for sulforaphane was observed at a concentration higher than 10 μM due to the toxic effects of sulforaphane.

Figure 2A:
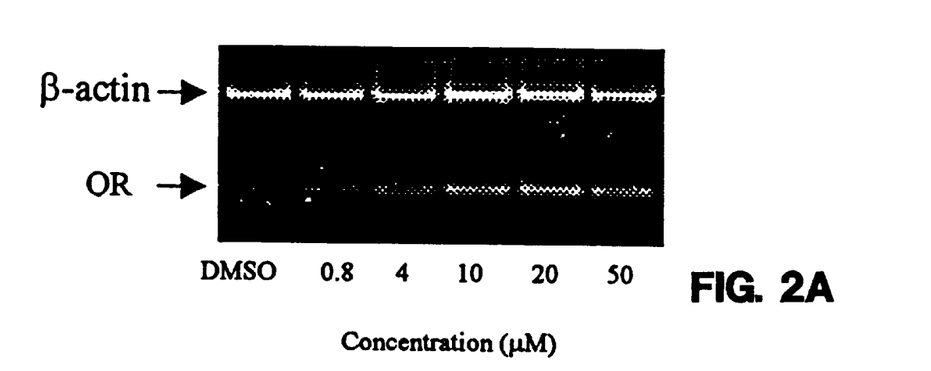
FIG. 2 shows RT-PCR analysis of QR mRNA levels in Hepa 1c1c7 cells after treatment with 4'-BF.
Figure 2B:
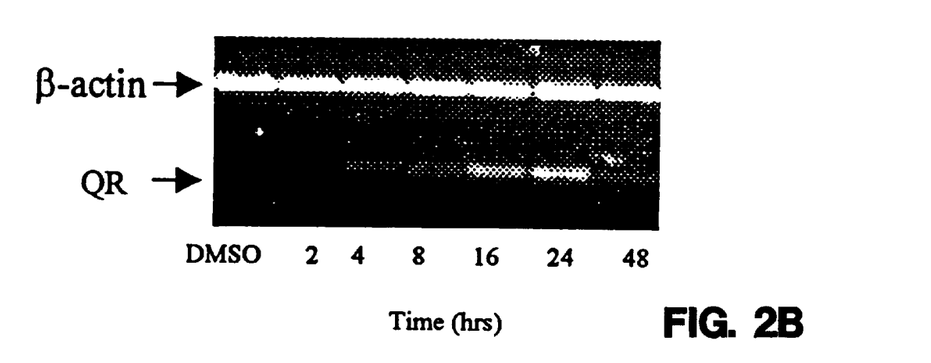

Induction of QR mRNA in Hepa 1c1c7 Cells. Transcriptional regulation of QR activity, as a monitor of phase II enzyme induction, was further demonstrated using RT-PCR. EHPA 1c1c7 cells were treated with 4'-BF (10 μM) or DMSO (solvent control) for 2, 4, 8, 16, 24, or 48 hours. As illustrated in FIG. 2, QR mRNA levels were increased after an 8-hour incubation period, reaching a maximum at 24 hours, and showing a decrease at 48 hours. Dose-dependent effects of 4'-BF were analyzed at the time of maximum induction (24 hours), and QR mRNA expression was induced in the concentration range of 0.8–50 μM. In particular, FIG. 2 illustrates RT-PCR analysis of QR mRNA levels in Hepa 1c1c7 cells after treatment with 4'-BF. In FIG. 2(A), Hepa 1c1c7 cells were treated with the indicated concentrations of 4'-BF for 24 hours. In FIG. 2(B), Hepa 1c1c7 cells were treated with 10 μM 4'-BF for the indicated periods of time. Reverse transcription was carried out by SuperScript II reverse transcriptase (Life Technologies, Inc.) and oligo(dT)$_{16}$. The cDNA was amplified with Advantage Klen Taq polymerase (Clontech) by using QR primers and β-acrin (internal control), aliquots of the PCR product were electrophoresed on 2.5% agarose gels (Bio-Rad), and PCR fragments were visualized with ethidium bromide staining.

The levels of QR mRNA were significantly increased by 4'-BF at various concentrations (0, 0.16, 0.8, 4, 10, 20, and 50 μM for 24 hours) in a dose-dependent manner. The level of QR mRNA was induced by 10 μM of 4'-BF after an 8 hour incubation time, with no significant differences from 8 to 24 hours.

Transcient Transfection of HepG2 Human Hepatoma Cells with QR Promoter-CAT Constructs. To determine the induction pattern and investigate the regulatory elements of QR gene mediated by 4'-BF, the induction of QR was analyzed in a transient transfection assay. Treatment with 10 μM of 4'-BF or 10 μM sulforaphane significantly (p<0.0001) induced CAT protein expression in HepG2 cells transfected with the pDTD-1097CAT construct or QR-ARE contruct. Significant induction of CAT protein expression in HepG2 cells transfected with QR-XRE was observed in response to treatment with 4'-BF, but was not observed in response to treatment with sulforaphane.

Figure 1:
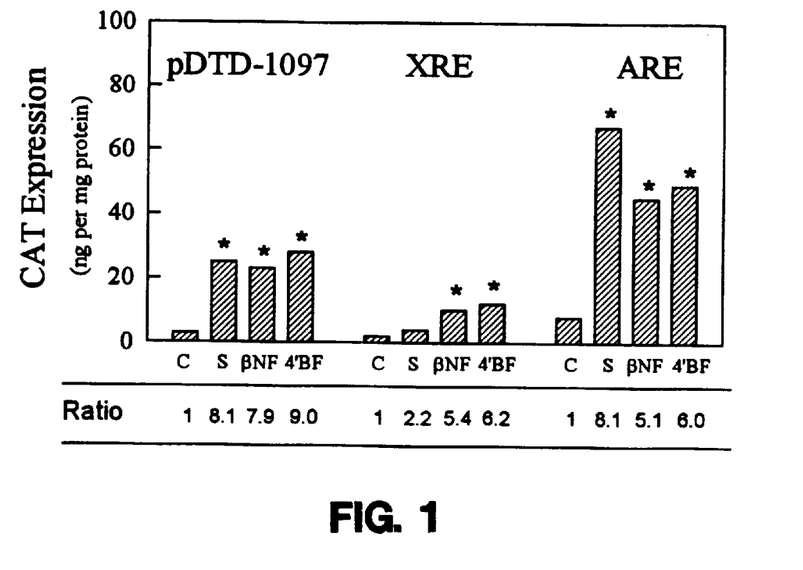
FIG. 1 contains bar graphs of CAT expression (ng/mg protein) in HepG2 cells transfected with QR-CAT constricts treated with sulforaphane, βNF, and 4'-BF.

On the basis of data obtained with mutant Hepa 1c1c7 cell lines (data not shown), 4'-BF was identified as a bifunctional inducer. This was further investigated in transient transfection experiments wherein human hepatoma cells were transfected with DNA constructs containing various portions of the 5' upstream promoter region of the QR gene linked to the CAT reporter gene by using the calcium phosphate precipitation method. Construct pDTD-1097CAT contains elements of the rat QR gene connected to the CAT construct gene. QR XRE-CAT consists of the XRE of the rat QR gene containing an Ah receptor recognition site connected to a heterologous promoter fused to the CAT gene, whereas QR ARE-CAT contains the ARE of the rat QR gene connected to the heterologous promoter fused to the CAT gene. As shown in FIG. 1, treatment with 4'-BF (10 μM) or βNF (10 μM; a well-known bifunctional inducer) significantly (P<0.0001, students t test with n=4) induced CAT expression via interaction with both the ARE and the XRE, whereas the monofunctional inducer, sulforaphane (10 μM), selectively interacted with the ARE.

In particular, FIG. 1 illustrates quantitation of CAT expression in HepG2 cells transfected with QR-CAT constructs. Transfected cells were treated with 10 μM sulforaphane (S), 10 μM βNF, 10 μM 4'-BF, or DMSO (0.5% final concentration) as control (C). Cells were transfected with pDTD-1097CAT, QR XRE-CAT, or QR ARE-CAT. CAT expression (ng CAT/mg protein) was determined using a CAT ELISA, and the ratio of CAT expression between treated and control cells was calculated (ratio=treated/control). These data indicate that 4'-BF, at least in part, binds to the Ah receptor, where its ligand complex is translocated to the nucleus, interacts with multiple copies of XRE, and transcriptionally activates the phase I cytochrome P4501A1 isozyme gene, as well as phase II enzyme genes.

Inhibition of DMBA-induced Mammary Tumor Carcinogenesis in Rat. Maximum dose tolerance (MDT) studies (data not included) were performed prior to conducting the chemopreventative studies of 4'-BF in animals. Briefly, a test agent was examined in a three-week study to determine the maximum dose that can be administered without causing suppression of body weight gain or inducing other gross manifestations of toxicity and to determine the effective dose in term of induction of phase II detoxifying enzymes. According to the MDT study, two doses of 4'-BF (2000 and 4000 mg/kg diet) were used for the chemopreventative studies. The chemopreventative study results demonstrated that dietary administration of 2000 or 4000 mg/kg of 4'-BF significantly decreased the DMBA-induced mammary tumor incidence from 88.9% to 25% or 15%, and the multiplicity from 2.75 to 0.20 or 0.15, respectively. Whereas the tumor latency was significantly increased (P<0.01), no significant differences in body weights among all groups of animals were observed. Dietary supplements of 4'-BF raised no clinical signs of toxicity or low survival rates in all groups (see FIG. 9).

lase to form reactive metabolites, notably, DMBA-3,4-diol-1,2-epoxide. DMBA itself induces phase I and phase II enzyme activities, as well.

Test animals were placed on various experimental diets for one week (Table 1) prior to a single i.g. dose of DMBA (15 mg). One day after DMBA was given, animals were

TABLE 2

Bioassay and Animal Data
Quinone Reductase Activity of Synthetic Flavonoids in Hepa 1c1c7 Cells

| Compound | $Cd^{a\ 1)}$ ($\mu$M) | $Cq^{b\ 2)}$ ($\mu$M) | $IC_{50}^{c\ 3)}$ ($\mu$M) | $Ci^{d\ 4)}$ ($IC_{50}$/CD) |
|---|---|---|---|---|
| Chalcone | NI | ND | 33 | ND |
| 2-Bromo-2'-hydroxychalcone | 0.53 | 2.0 | 11 | 21 |
| 2'-Hydroxy-2-methoxychalcone | 0.31 | 1.8 | 17 | 55 |
| 2'-Hydroxy-2,6-dimethoxychalcone | 0.53 | 3.7 | 14 | 26 |
| 2'-Hydroxy-2-methylchalcone | 0.67 | 9.0 | 36 | 54 |
| 2'-Hydroxy-2-nitrochalcone | 0.30 | 3.6 | 11 | 37 |
| 2'-Hydroxy-3-trifluoromethylchalcone | <0.55 | 0.55 | 12.8 | >23 |
| 2'-Hydroxy-4-trifluoromethylchalcone | <0.55 | 1 | 55 | >100 |
| 4'-Bromoflavanone | 2.3 | 11 | 63 | 27 |
| 2'-Methoxyflavanone | 0.63 | 6.9 | >79 | >125 |
| 2'-Methylflavanone | 1.0 | 6.8 | 81 | 81 |
| 1'-Naphthylflavanone | 1.8 | 8.6 | 43 | 24 |
| Flavone | 2.5 | 8.3 | 106 | 42 |
| 3'-Bromoflavone | 0.1 | 4.4 | 3.2 | 32 |
| 4'-Bromoflavone | 0.01 | 0.15 | >166 | >17000 |
| 3'-Chloroflavone | <0.58 | toxic | 23 | >40 |
| 4'-Chloroflavone | 0.016 | 0.66 | >78 | >5000 |
| 2'-Fluoroflavone | 0.8 | 10 | >83 | 104 |
| 3'-Fluoroflavone | 0.67 | 1.24 | 42 | 63 |
| 4'-Fluoroflavone | 3.4 | 32 | >83 | >24 |
| 4'-Trifluoromethylflavone | 0.03 | 0.1 | 90 | 3000 |
| 3-Bromo-2'-hydroxychalcone | 1.3 | 8.2 | 21 | 16 |
| 4-Bromo-2'-hydroxychalcone | 18 | 66 | 66 | 4 |
| Sulforaphone | 0.43 | | 11 | 26 |

NI: No induction
ND: Not determined
1)Mean value of the concentration to double the specific activity of QR ($\eta$ = 2–4) in Hepa 1c1c7 cells
2)Mean value of the half-maximal inhibitory concentration of Hepa 1c1c7 cell viability (n = 4)
3)Concentration for 50% cell survival after incubation with test compound
4)Chemoprevention index, defined as $IC_{50}$/CD

TABLE 3

Induction of Quinone Reductase (QR) and
Glutathione (GSH) in Mouse Liver and Mammary Glands

| | QR (Treated/Control) Liver | Mammary Gland | GSH (Treated/Control) Liver | Mammary Gland |
|---|---|---|---|---|
| 4'-Bromo-flavone | 5.27 | 2.66 | 2.11 | 1.77 |

Figure 3A:
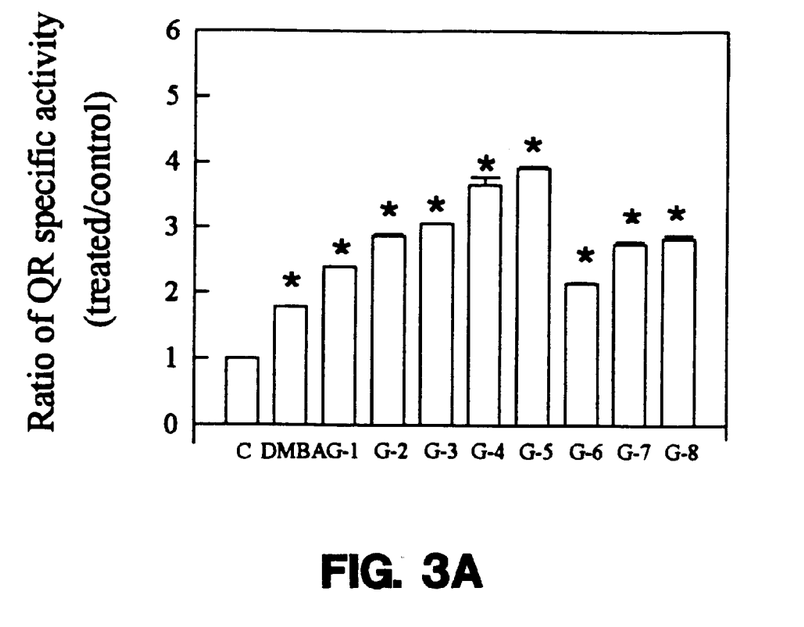
FIG. 3 contains bar graphs showing the effect of 4'-BF on DMBA-induced QR activity in mammary gland (A) and liver (B)
Figure 3B:
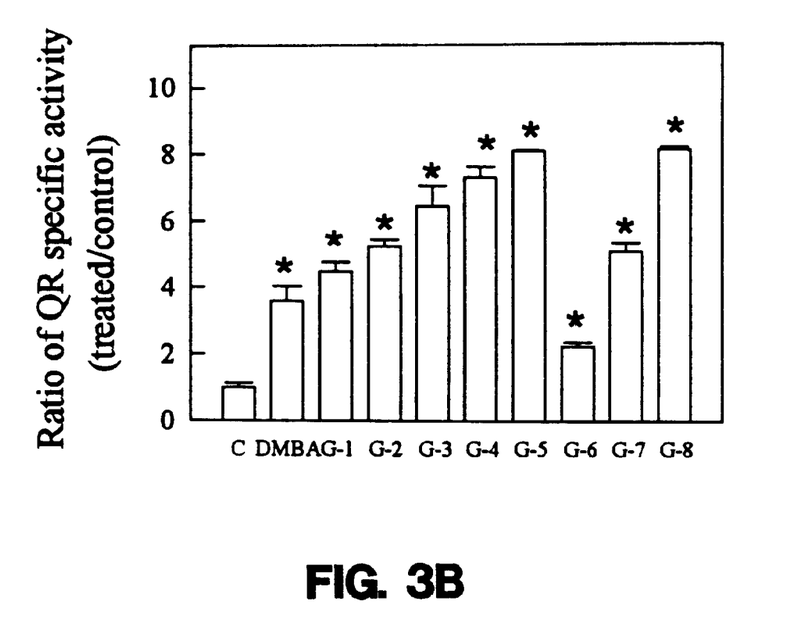
Figure 4A:
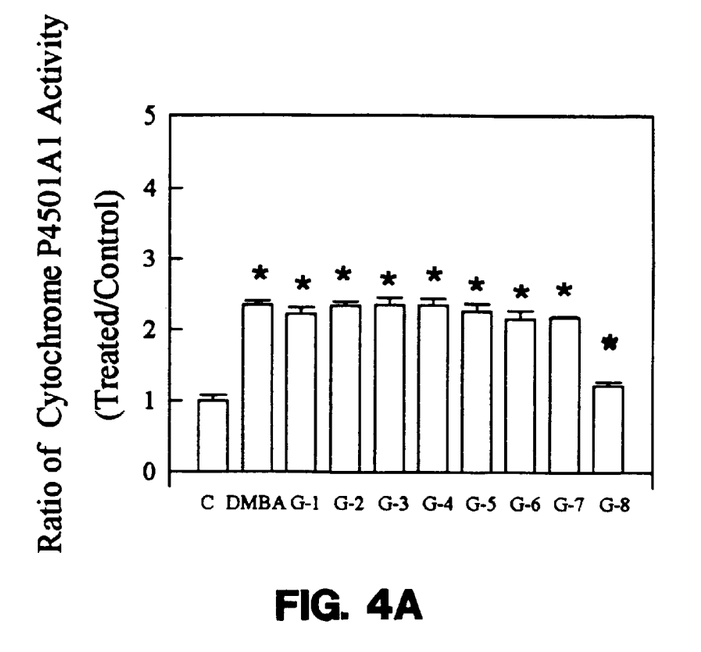
FIG. 4 contains bar graphs showing the effect of 4'-BF on DMBA-induced cytochrome P4501A1 activity in mammary gland (A) and liver (B)
Figure 4B:
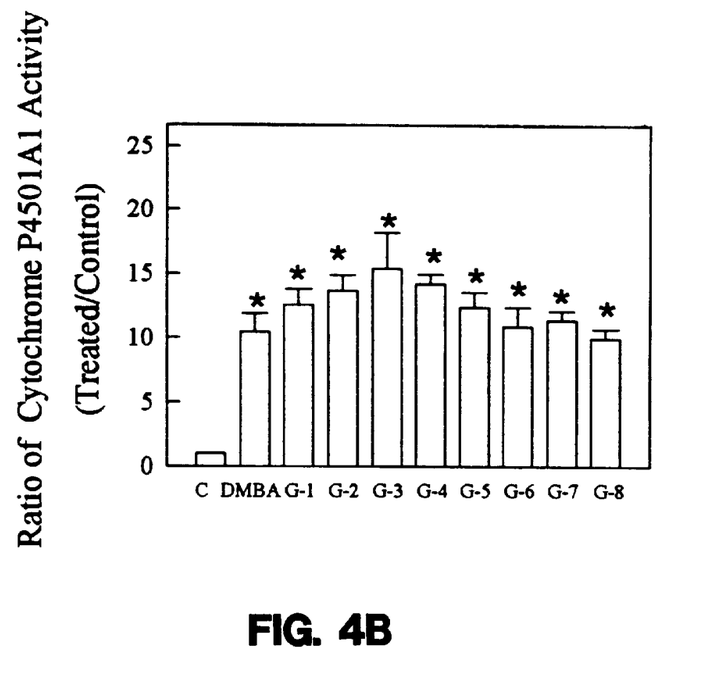

Phase I enzyme induction is considered a potential cancer risk factor due to the activation of procarcinogens to their ultimate reactive forms. Therefore, the relative induction of phase I and phase II enzyme activities by 4'-BF can be of critical importance. In the case of βNF, a flavonoid bifunctional inducer with activity similar to 4'-BF, it has been shown that induction of cytochrome P450 isozymes can enhance or reduce tumorigenesis. To explore this issue, the effect of 4'-BF on DMBA-induced QR (phase II enzyme) and cytochrome P4501A1 (phase I enzyme) activities in rat liver and mammary gland was investigated. DMBA is a potent carcinogen that is selectively active in sites such as the mammary gland and skin, and has been widely used as a prototype carcinogen in experimental animal models. To exert its carcinogenic effect, DMBA undergoes bioactivation which involves cytochrome P4501A1 and epoxide hydrosacrificed, and tissues were collected. QR activity and cytochrome P4501A1 activity were then assessed in the liver and mammary gland. As indicated in FIGS. 3 and 4, in liver and mammary gland, both QR and cytochrome P4501A1 activities were significantly induced in comparison with the control groups (basal diet) by each treatment regimen, except cytochrome P4501A1 activity in mammary gland with treatment by 4'-BF (5000 mg/kg diet) alone. However, treatment with 4'-BF in addition to DMBA did not significantly alter DMBA-induced cytochrome P4501A1 activities in either liver or mammary gland (FIG. 4). On the other hand, significant dose-dependent induction of QR activity was observed on treatment with either DMBA and 4'-BF or 4'-BF alone, compared to treatment by DMBA alone, in liver and mammary gland. These results suggest that as the dose of 4'-BF increased, induction of phase II enzyme expression in rat liver and mammary gland was more favorable, as compared with phase I enzyme induction.

Figure 5:
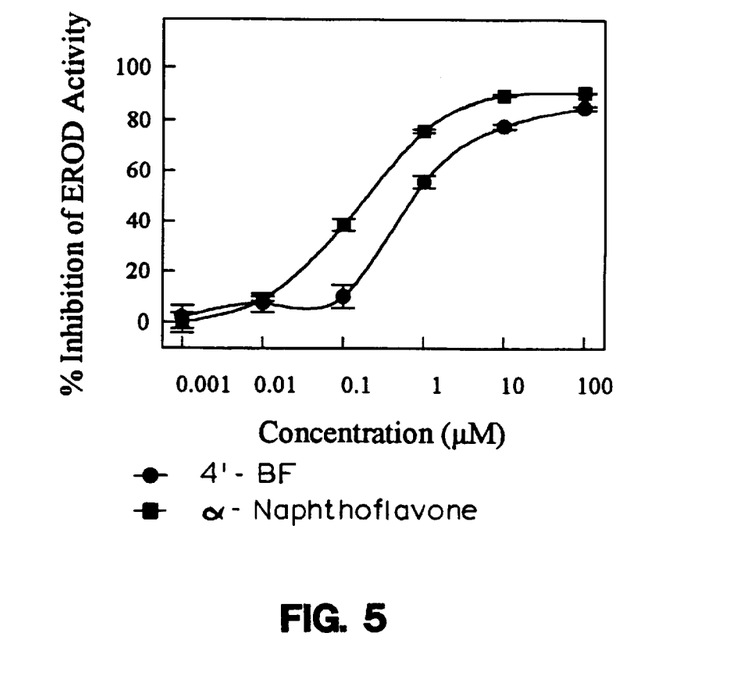
FIG. 5 contains plots of % inhibition of cytochrome P4501A1-mediated EROD activity using liver microsomes derived from DMBA-treated rats.

Furthermore, 4'-BF can significantly inhibit TCDD (tetrachlorodibenzo-p-dioxin)-induced EROD activity (phase I cytochrome P4501A1). A similar inhibitory effect of 4'-BF on cytochrome P4501A1-mediated EROD activity was observed using microsomes derived from the liver of DMBA-treated rats. As shown in FIG. 5, 4'-BF mediated an inhibitory response with an $IC_{50}$ of 0.86 $\mu$M. A comparable profile was observed with a-naphthoflavone ($IC_{50}$ of 0.09 $\mu$M), a well-known cytochrome P4501A1 inhibitor. Consistent with this activity, 4'-BF strongly inhibits DMBA-induced mutagenesis with *Salmonella typhimurium* strain TM677 (data not shown), most likely due to direct inhibition of cytochrome P4501A1. Therefore, it is theorized that 4'-BF binds to the Ah receptor, interacts with the XRE, and transcriptionally activates the cytochrome P4501A1 gene. In addition, however, 4'-BF also can function as a competitive inhibitor that binds to and blocks the activity of cytochrome P4501A1.

Figure 6:
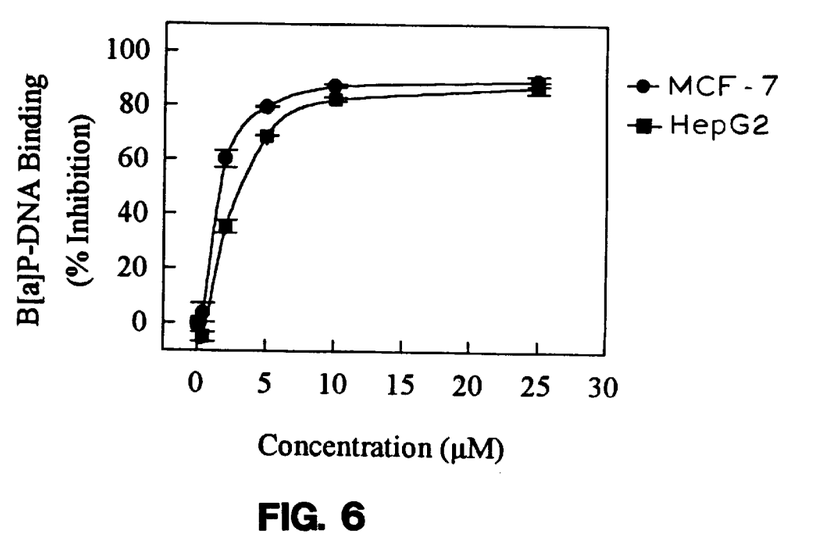
FIG. 6 contains plots of % inhibition of binding of B [a] P-DNA metabolites to DNA or MCF-7, or HepG2 cells in culture.

To assess the functional significance of the net modulation of phase I and phase II enzyme activities mediated by 4'-BF, the effect of 4'-BF on the binding of metabolically activated B[α]P to the genomic DNA of cultured MCF-7 or HepG2 cells was determined. A favorable effect on the expression of phase II enzymes probably enhances metabolic detoxification, decreases the availability of carcinogen reactive metabolites capable of interacting with DNA, and thereby provides a chemoprotective effect. As illustrated in FIG. 6, 4'-BF inhibited the formation of B[α]P-DNA adducts with $IC_{50}$s of about 1.7 and 3.1 $\mu M$ with cultured MCF-7 cells and HepG2 cells, respectively.

Figure 9A:
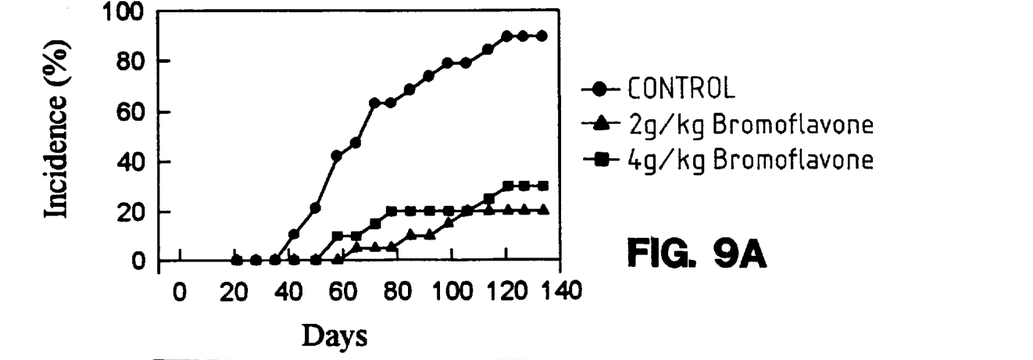
FIG. 9A contains plots of total observable mammary tumors vs. time for control rats and for rats treated with 4'-bromoflavone.
Figure 9B:
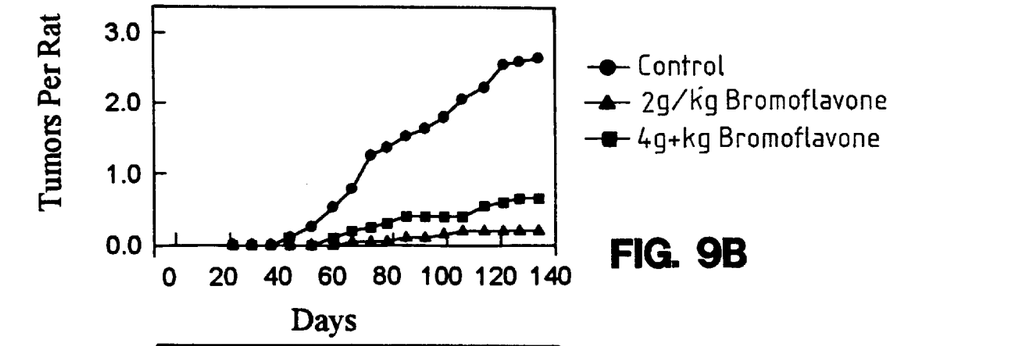
FIG. 9B contains plots of percent incidence of mammary tumors vs. time for control rats and for rats treated with 4'-bromoflavone.
Figure 9C:
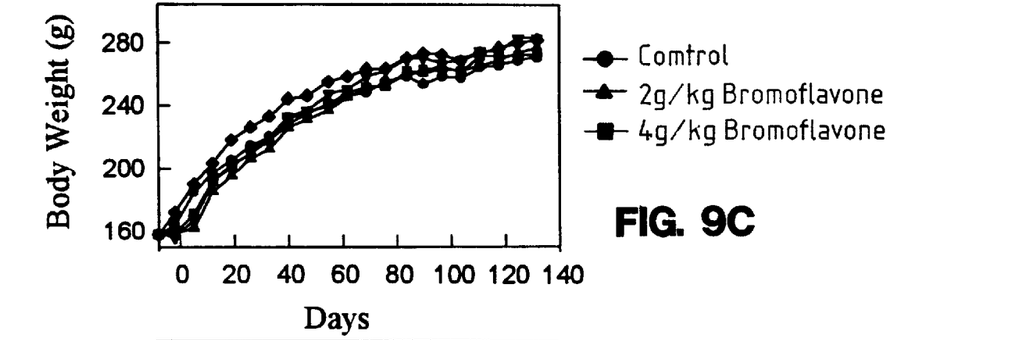
FIG. 9C contains plots of body weight vs. time for control rats and for rats treated with 4'-BF.
Figure 9D:
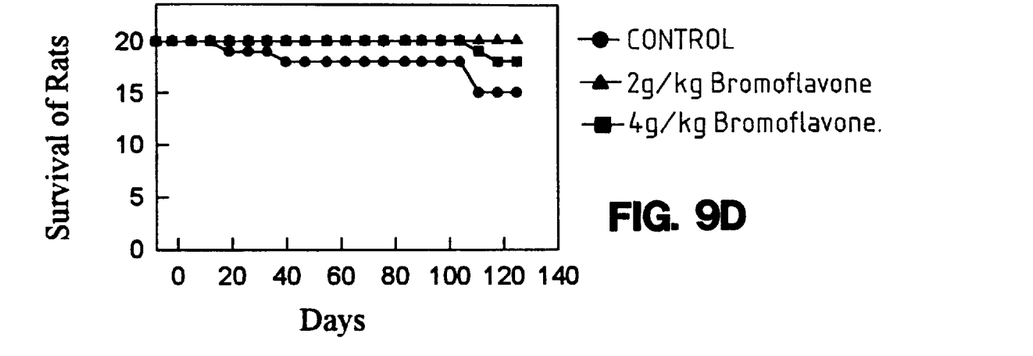
FIG. 9D contains plots of survival of rats vs. time for control rats and for rats treated with 4'-BF.

4'-BF also was evaluated and found to be a highly effective chemopreventive agent in the DMBA-induced rat mammary tumorigenesis model. As shown in FIG. 9, A and B, administration of 2000 or 4000 mg 4'-BF/kg diet significantly decreased tumor incidence from 89.5 to 30 and 20%, and multiplicity from 2.63 to 0.65 and 0.20 tumors/rat, respectively. Tumor latency also was enhanced greatly by administration of either dose of 4'-BF. There were no significant differences in body weight (FIG. 9C), and dietary supplementation improved survival (FIG. 9D).

4'-BF is a highly effective and novel cancer chemopreventive agent. The compound significantly induces phase II detoxification enzymes and exhibits low toxicity with in vitro and in vivo models. Because it is well known that DMBA requires bioactivation by cytochrome P4501A1 to exert its carcinogenic effect, it is theorized that the chemopreventive activity of 4'-BF is achieved by modification of carcinogen metabolism (inhibition of cytochrome P4501A1), increases in carcinogen excretion (induction of phase II detoxification enzymes), and decreases in carcinogen-DNA interactions. In addition to protection against DMBA-induced mammary tumorigenesis, the data illustrates that 4'-BF can be an effective inhibitor in other organ sites wherein phase II detoxification enzymes are induced. In addition, 4'-BF is a highly active chemopreventive agent that can be economically synthesized in mass quantities using readily available starting materials.

The above tests and data show the 4'-bromoflavone can be administered to mammals as a therapeutic or prophylactic against chemically induced cancers. 4'-Bromoflavone can be formulated as a pharmaceutical composition together with a pharmaceutically acceptable diluent or carrier, or with suitable excipients. Such diluents, carriers, and excipients are well known in the art. 4'-BF also can be used in combination with a second therapeutic agent useful in the treatment or prevention of cancer. The 4'-bromoflavone typically is present in such formulations in an amount of about 0.1% to about 75% by weight.

A combination of 4'-BF and a second therapeutic agent can be in the form of a pharmaceutical composition, typically further comprising a diluent, carrier, or excipient. The 4'-BF and second therapeutic agent also can be administered sequentially or simultaneously from separate pharmaceutical formulations. Appropriate doses of a second therapeutic agent for use in combination with 4'-BF is readily determined by persons skilled in the art.

Pharmaceutical compositions containing 4'-bromoflavone are suitable for administration to humans or other mammals. Typically, the pharmaceutical compositions are sterile, and contain no toxic, carcinogenic, or mutagenic compounds which would case an adverse reaction when administered.

Administration of 4'-bromoflavone can be performed before, during, or after exposure to a carcinogen or procarcinogen. 4'-BF can be administered by any suitable route, for example, by oral, buccal, sublingual, rectal, vaginal, nasal, topical, or parenteral (including intravenous, intramuscular, subcutaneous, and intracoronary) administration. Oral administration is preferred.

For human use, 4'-BF can be administered alone, but generally is administered in admixture with a pharmaceutical carrier selected with regard to the intended route of administration and standard pharmaceutical practice. For example, 4'-BF can be administered orally, buccally, or sublingually, in the form of tablets containing excipients such as starch or lactose, or in capsules or ovules, either alone or in admixture with excipients, or in the form of elixirs or suspensions containing flavoring or coloring agents. Such liquid preparations may be prepared with pharmaceutically acceptable additives, such as suspending agents. 4'-BF also can be injected parenterally, for example, intravenously, intramuscularly, subcutaneously, or intracoronarily. For parenteral administration, 4'-BF preferably is administered in the form of a sterile aqueous solution, which can contain other substances, for example salts, or monosaccharides, such as mannitol or glucose, to make the solution isotonic with blood.

Suitable doses to be administered are sufficient to induce a measurable increase of phase II enzymes. The dosage of 4'-bromoflavone typically does not exceed 500 $\mu$mol per kg per day, but can be much lower. Preferred dosages of 4'-bromoflavone are about 0.005 to about 1 $\mu$mol per kg per day. To achieve the full advantage of the present invention, 4'-bromoflavone is administered in a dosage of about 0.05 to about 0.75 $\mu$mol per kg per day, especially about 0.075 to about 0.5 $\mu$mol per kg per day. In practice, a physician determines the actual dosing regimen that is most suitable for an individual patient, and the dosage may vary with the age, weight, and response of the particular patient. The above dosages illustrate the average case, but there can be individual instances in which a higher or lower dosage is merited, and such are within the scope of this invention.

4'-Bromoflavone, therefore, can be easily and economically synthesized, and used in drug formulations as a cancer chemopreventative agent. Alternatively, 4'-bromoflavone can be added to food products as a cancer chemopreventative additive or supplement.

Many modifications and variations of the invention as herein before set forth can be made without departing from the spirit and scope thereof, and only such limitations should be imposed as are indicated by the appended claims.

What is claimed is:

1. A method of chemopreventing a cancer sensitive to 4'-bromoflavone, said method comprising administering a sufficient amount of a cancer chemopreventative composition comprising 4'-bromoflavone to a mammal in need thereof to prevent, delay, or reverse a cancer sensitive to 4'-bromoflavone.

2. The method of claim 1 wherein the composition is a solid.

3. The method of claim 1 wherein the composition is a liquid.

4. The method of claim 1 wherein the composition is administered topically.

5. The method of claim 1 wherein the composition is administered orally.

6. The method of claim 1 wherein the composition is administered parenterally.

7. The method of claim 1 wherein the composition is administered buccally or sublingually.

8. The method of claim 1 wherein the composition is administered nasally.

9. The method of claim 1 wherein the composition is administered vaginally or rectally.

10. The method of claim 1 wherein the composition is a food additive.

11. The method of claim 1 wherein the composition is a pharmaceutical.

12. The method of claim 1 wherein the composition is administered in an amount of about 0.005 to about 1 micromoles per kg per day.

13. The method of claim 1 wherein the composition is administered in an amount of about 0.05 to about 0.75 micromoles per kg per day.

14. The method of claim 1 wherein the composition is administered in an amount of about 0.075 to about 0.5 micromoles per kg per day.

15. The method of claim 1 wherein the composition is administered prior to exposure of the mammal to a carcinogen or a procarcinogen.

16. The method of claim 1 wherein the composition is administered during or after exposure of the mammal to a carcinogen or a procarcinogen.

17. The method of claim 1 wherein the mammal is a human.

18. The method of claim 1 wherein the cancer chemopreventative composition induces a measurable increase of phase II enzymes in the mammal.

* * * * *